(12) United States Patent
Matson et al.

(10) Patent No.: US 11,041,847 B1
(45) Date of Patent: Jun. 22, 2021

(54) DETECTION AND MODIFICATION OF GUT MICROBIAL POPULATION

(71) Applicant: IXCELA, INC., Bedford, MA (US)

(72) Inventors: Wayne R. Matson, Ayer, MA (US); Samantha A. Matson, Groton, MA (US); Erika N. Ebbel-Angle, Beverly, MA (US); Srikant Sarangi, Cambridge, MA (US)

(73) Assignee: IXCELA, INC., Bedford, MA (US)

( * ) Notice: Subject to any disclaimer, the term of this patent is extended or adjusted under 35 U.S.C. 154(b) by 0 days.

(21) Appl. No.: 16/859,453

(22) Filed: Apr. 27, 2020

Related U.S. Application Data (63) Continuation-in-part of application No. 16/258,199, filed on Jan. 25, 2019.

(51) Int. Cl.
| | | |
|---|---|---|
| *G01N 33/50* | (2006.01) | |
| *G16H 20/30* | (2018.01) | |
| *G16H 20/60* | (2018.01) | |
| *G01N 33/487* | (2006.01) | |
| *G16H 20/10* | (2018.01) | |
| *G16H 50/20* | (2018.01) | |

(52) U.S. Cl.
CPC ....... *G01N 33/5038* (2013.01); *G01N 33/487* (2013.01); *G16H 20/10* (2018.01); *G16H 20/30* (2018.01); *G16H 20/60* (2018.01); *G16H 50/20* (2018.01); *G01N 2800/52* (2013.01)

(58) Field of Classification Search
CPC ............. G01N 33/487; G01N 33/5038; G01N 2800/52; G16H 20/10; G16H 20/30; G16H 20/60; G16H 50/20
See application file for complete search history.

(56) References Cited

U.S. PATENT DOCUMENTS

| | | | |
|---|---|---|---|
| 4,201,646 A | 5/1980 | Matson | 204/195 H |
| 4,233,031 A | 11/1980 | Matson et al. | 23/230 B |
| 4,288,303 A | 9/1981 | Matson | 204/105 R |
| 4,404,065 A | 9/1983 | Matson | 204/1 T |
| 4,497,199 A | 2/1985 | Matson | 73/61.1 C |
| 4,511,659 A | 4/1985 | Matson | 436/150 |
| RE32,920 E | 5/1989 | Matson et al. | 204/1 T |

(Continued)

FOREIGN PATENT DOCUMENTS

| | | | |
|---|---|---|---|
| CN | 1292693 | 4/2001 | ........... A61K 31/403 |
| CN | 102961521 | 3/2013 | ............. A61K 35/64 |

(Continued)

OTHER PUBLICATIONS

Zhao et al. (Metabolomics, 2010, 6:362-374) (Year: 2010).*

(Continued)

*Primary Examiner* — Jeremy C Flinders
(74) *Attorney, Agent, or Firm* — Hayes Soloway P.C.

(57) ABSTRACT

Methods and systems for evaluating heath/disease state of an individual are provided herein. In particular, the disclosure provides methods for measuring levels of one or more metabolites of interest in an individual and using these measurements to assess the individual's health. The disclosure also provides systems for carrying out the disclosed methods. For example, the disclosed systems may include a metabolite level evaluation module to determine the individual's heath based on the metabolite levels measured.

6 Claims, 6 Drawing Sheets

(56) References Cited

U.S. PATENT DOCUMENTS

| | | | | |
|---|---|---|---|---|
| 4,863,873 | A | 9/1989 | Matson | 436/63 |
| 5,104,639 | A | 4/1992 | Matson | 424/2 |
| 5,501,836 | A | 3/1996 | Myerson | 422/57 |
| 6,194,217 | B1 | 2/2001 | Matson | 436/63 |
| 6,210,970 | B1 | 4/2001 | Matson | 436/64 |
| 6,395,768 | B1 | 5/2002 | Pappolla et al. | 514/415 |
| 6,475,799 | B1 | 11/2002 | Matson | 436/8 |
| 6,548,252 | B1 | 4/2003 | Matson | 435/6 |
| 6,558,955 | B1 | 5/2003 | Kristal et al. | 436/63 |
| 6,585,937 | B1 | 7/2003 | Matson | 422/69 |
| 7,214,486 | B2 | 5/2007 | Matson | 435/6 |
| 7,297,481 | B2 | 11/2007 | Matson | 435/6 |
| 7,626,017 | B2 | 12/2009 | Laugham | B01L 3/502753 |
| 7,734,420 | B2 | 6/2010 | Palsson et al. | 702/19 |
| 7,972,781 | B2 | 7/2011 | Matson | 435/6 |
| 8,679,457 | B2 | 3/2014 | Alexander | G01N 33/564 |
| 9,603,837 | B2 | 3/2017 | Matson | A61K 31/405 |
| 9,636,325 | B2 | 5/2017 | Matson | A61K 31/405 |
| 9,910,047 | B2 * | 3/2018 | Gall | G06F 19/00 |
| 2003/0207307 | A1 | 11/2003 | Matson | 435/6.11 |
| 2004/0029830 | A1 | 2/2004 | Hebert | 514/55 |
| 2004/0053319 | A1 | 3/2004 | McWilliams | 435/6.18 |
| 2005/0287197 | A1 | 12/2005 | Kurtz | 424/450 |
| 2006/0008464 | A1 | 1/2006 | Gilon | 424/185.1 |
| 2006/0018832 | A1 | 1/2006 | Bates | 424/9.1 |
| 2007/0105937 | A1 | 5/2007 | Pappolla et al. | 514/419 |
| 2007/0128298 | A1 | 6/2007 | Cowley | 424/722 |
| 2008/0161228 | A1 | 7/2008 | Ryals et al. | 514/2 |
| 2008/0207731 | A1 | 8/2008 | Rogers | 514/419 |
| 2009/0047667 | A1 | 2/2009 | Wong | 435/6.13 |
| 2010/0074969 | A1 | 3/2010 | Hughes | 31/736 |
| 2010/0144836 | A1 | 6/2010 | Van Engeland et al. | 514/44 A |
| 2010/0172874 | A1 | 7/2010 | Turnbaugh et al. | 424/93.4 |
| 2010/0317710 | A1 | 12/2010 | Rogers | 514/419 |
| 2011/0010099 | A1 | 1/2011 | Adourian et al. | 702/19 |
| 2011/0263540 | A1 | 10/2011 | Pang et al. | A61K 31/04 |
| 2011/0319387 | A1 | 12/2011 | Schmidt et al. | 514/215 |
| 2012/0022234 | A1 | 1/2012 | Bousquet-Gagnon et al. | 530/358 |
| 2012/0238028 | A1 | 9/2012 | Reszka et al. | 436/71 |
| 2012/0258874 | A1 | 10/2012 | Narain et al. | 506/8 |
| 2013/0115670 | A1 | 5/2013 | Nazareth | B01L 7/52 |
| 2013/0267469 | A1 | 10/2013 | Matson | 514/16.4 |
| 2013/0330824 | A1 | 12/2013 | Li | 435/375 |
| 2016/0320367 | A1 | 11/2016 | Matson et al. | G01N 33/49 |
| 2018/0264053 | A1 | 9/2018 | Lynch | A61K 39/02 |

FOREIGN PATENT DOCUMENTS

| | | | | |
|---|---|---|---|---|
| CN | 103800485 | | 5/2014 | A61K 35/64 |
| EP | 2218792 | | 8/2010 | C12Q 1/68 |
| JP | H11103832 | | 4/1999 | A23F 3/14 |
| JP | 2001502792 | | 2/2001 | G01N 27/62 |
| JP | 2006503373 | | 1/2006 | G01N 33/50 |
| WO | WO 03004486 | | 1/2003 | C07D 311/76 |
| WO | WO 2005036180 | | 4/2005 | G01N 33/68 |
| WO | WO 2005062851 | | 7/2005 | A01N 25/00 |
| WO | WO 2008024914 | | 2/2008 | A61K 31/405 |
| WO | WO 2013012332 | | 1/2013 | C12Q 1/10 |
| WO | WO 2013148709 | | 10/2013 | A61K 31/405 |
| WO | WO-2018136884 | A1 * | 7/2018 | A61K 31/198 |

OTHER PUBLICATIONS

Fu et al. (Biopharmaceutical Report, vol. 26, No. 2—Summer2019) (Year: 2019).*

生物医学工程的基础与临床 93-103, 1989 (no translation available)(20 pgs).

Anderson, George, "Quantitation of tryptophan metabolites in rat feces by thin-layer chromography", *Journal of Chromatography*, 105 (1975) 323-328 (6 pgs).

Angle, E., "Development and Implementation of New Techniques to Study Biomarkers in Huntington Disease," PhD diss., Boston University, 2012 (261 pgs).

Bendheim et al., "Development of indole-3-propionic acid (OXIGON) for Alzheimer's disease," J Mol Neurosci. Aug.-Oct. 2002;19(1-2):213-7. Review. PMID (5 pgs).

Bertini et al., The Metabonomic Signature of Celiac Disease, Journal of Proteome Research 2009, vol. 8, pp. 170-177 (8 pgs).

Bird et al., "Structural characterization of plasma metabolites detected via LC-electrochemical coulometric array using LC-UV fractionation, MS, and NMR," Anal. Chem. Nov. 20, 2012;84(22):9889-98. doi: 0.1021/ac302278u. Epub Nov. 6, 2012 (10 pgs).

Blech et al., "The Metabolism and Disposition of the Oral Direct Thrombin Inhibitor, Dabigatran, In Humans," 2008; 36: 386-399 (14 pgs).

Bogdanov et al., "Increased Oxidative Damage to DNA in ALS Patients," Free Radical Biology & Medicine. Oct. 1, 2000; 29(7): 652-658 (7 pgs).

Bogdanov et al., "Metabolomic profiling to develop blood biomarkers for Parkinson's disease," Brain. Feb. 2008; 389-396 (8 pgs).

Borland et al., "An Introduction to Electrochemical Methods in Neuroscience," Electrochemical Methods for Neuroscience, Boca Raton (FL): CRC Press/Taylor & Francis; 2007 (18 pgs).

Borovecki et al., Genome-wide expression profiling of human blood reveals biomarkers for Huntington's disease, PNAS, 2005; 102: 11023-11028 (6 pgs).

Bumb et al., "Macromolecular and Dendrimer Based Magnetic Resonance Contrast Agents," NIH Public Access Author Manuscript, 2010, pp. 1-28 (28 pgs).

Burns et al., Clinical practice with anti-dementia drugs: a consensus statement from British Association for Psychopharmacology, J Psychopharmacol. 2006; 20: 732-55 (24 pgs).

Canadian Office Action issued in application No. 2,868,451, dated Mar. 1, 2019 (4 pgs).

Canadian Office Action issued in application No. 2,868,451, dated Jan. 23, 2020 (3 pgs).

Canadian Office Action issued in application No. 2,917,231, dated Jul. 20, 2020 (5 pgs).

Carreterro et al., "Clay and non-clay minerals in the pharmaceutical industry: Part I. Excipients and medical applications," Applied Clay Science, 2009, vol. 46, pp. 73-80 (8 pgs).

Casiday et al., The Washington University at St. Louis website, downloaded Sep. 21, 2018, (http://www.chemistry.wustl.edu/~edudev/LabTutorials/Hemoglobin/MetalComplexinBlood.html; hereafter, the hemoglobin website) 2018 (15 pgs).

Caudle et al., "Using 'omics' to define pathogenesis and biomarkers of Parkinson's disease," Expert Review of Neurotherapeutics, vol. 10, No. 6, Jun. 1, 2010, pp. 925-942 (29 pgs).

Chiaro et al. (Sci. Transl. Med., 2017, 9, eaaf9044) (Year: 2017) (12 pgs).

Chinese Notice of Reexamination (w/machine translation)issued in application No. 201480037986.8, dated Apr. 28, 2020 (10 pgs).

Chinese Office Action (w/machine translation)issued in application No. 201480037986.8, dated Feb. 20, 2019 (20 pgs).

Chinese Office Action (w/translation) issued in application No. 201480037986.8, dated Feb. 11, 2018 (21 pgs).

Chinese Office Action (w/translation) issued in application No. 201480037986.8, dated Aug. 8, 2018 (19 pgs).

Chinese Office Action (w/translation) issued in application No. 201380023926.6, dated Oct. 22, 2018 (18 pgs).

Chinese Office Action (w/translation) issued in application No. 201380023926.6, dated Oct. 25, 2017 (11 pgs).

Chinese Office Action (w/translation) issued in application No. 201380023926.6, dated Jan. 29, 2019 (8 pgs).

Chinese Office Action (w/translation) issued in application No. 201580006282.9, dated Apr. 2, 2019 (11 pgs).

Chinese Office Action (w/translation) issued in application No. 201580006282.9, dated Nov. 13, 2019 (9 pgs).

Chinese Office Action (w/translation) issued in application No. 201580006282.9, dated Jun. 12, 2020 (9 pgs).

Chinese Office Action issued in application No. 201380023926.6, dated Sep. 22, 2015 (9 pgs).

(56) References Cited

OTHER PUBLICATIONS

Chinese Office Action issued in application No. 201380023926.6, dated May 31, 2016 (9 pgs).
Chinese Office Action issued in application No. 201380023926.6, dated Nov. 22, 2016 (11 pgs).
Chinese Office Action issued in application No. 201380023926.6, dated Apr. 18, 2017 (11 pgs).
Chung, MCM, "Structure and Function of Transferrin," 1984, Biochemical Education, vol. 12, issue 4, pp. 146-154 (9 pgs).
Chyan et al., "Potent Neuroprotective Properties against the Alzheimer β-Amyloid by an Endogenous Melatonin-related Indole Structure, Indole-3-propionic Acid," Journal of Biological Chemistry. Jul. 30, 1999; 274(31): 21937-21942 (6 pgs).
Clark, J., The website on Coordinate Covalent Bonds, downloaded Sep. 7, 2018, https://chem.libretexts.org/Textbook_Maps/Physical_and_Theoretical_Chemistry_Textbook_Maps/Supplemental_Modules_(Physical_and_Theoretical_Chemistry)/Che, 2018 (4 pgs).
Cook et al., Pharmacokinetics and Metabolism of [$^{14}$C]eplerenone After Oral Administration to Humans, 2003; 31:1448-1455 (8 pgs).
Crider et al., Folate and DNA Methylation: A Review of Molecular Mechanisms and the Evidence for Folate's Role, Advances in Nutrition, 2012, 3, 21-38 (18 pgs).
Ebbel et al., "Identification of Phenylbutyrate-Generated Metabolites in Huntington Disease Patients using Parallel LC/EC-array/MS and Off-line Tandem MS," Anal Biochem. Apr. 15, 2010; 399(2): 152-161 (20 pgs).
El-Ansary et al., "Biomarker Discovery in Neurological Diseases: A Metabolomic Approach," Open Access Journal of Clinical Trials, Nov. 30, 2009, vol. 1, pp. 27-41 (15 pgs).
Elsadek et al., "Impact of albumin on drug delivery—New applications on the horizon," Journal of Controlled Release, vol. 157, 2012, pp. 4-28 (25 pgs).
Epping et al., "Depression in the early stages of Huntington disease," Author Manuscript, NIH Public Access, 2012, 1-11, 2012 (11 pgs).
European Office Action issued in application No. 13 768 233.2, dated Apr. 3, 2018 (6 pgs).
European Office Action issued in application No. 13 768 233.2, dated Mar. 4, 2019 (6 pgs).
European Office Action issued in application No. 13768233.2, dated Oct. 27, 2015 (7 pgs).
European Office Action issued in application No. 15 742 641,2, dated Feb. 15, 2019 (5 pgs).
European Search Report issued in application 14820565.1, dated Feb. 6, 2017 (10 pgs).
European Official Action issued in application No. 15742641.2, dated May 26, 2020 (4 pgs).
European Search Report issued in application No. 15742641.2, dated Jun. 28, 2017 (15 pgs).
European Search Report issued in application No. 15742641.2, dated Sep. 21, 2017 (16 pgs).
European summons to attend oral proceedings issued in application No. 14820565.1, dated Jun. 6, 2019 (16 pgs).
Extended European search report issued in application No. 13768233.2, dated Dec. 22, 2015 (15 pgs).
Gavett et al., Author Manuscriptof Clin Sports Med. Jan. 2011; 30(1): 179-xi. doi: 10.1016/j.csm.2010.09.007; 10 pages.
Gordis, L., Epidemiology, Second Edition, 2000 WB Saunders Company, Chapter 4, "Assessing the Validity and Reliability of Diagnostic and Screening Tests," pp. 63-80 (19 pgs).
Gurova, K., "New hopes from old drugs: revising DNA-binding small molecules as anticancer agents," NIH Public Access, Author Manuscript, 2009, 1-28 (28 pgs).
Haes et al., Detection of a Biomarker for Alzheimer's Disease from Synthetic and Clinical Samples Using a Nanoscale Optical Biosensor, Journal of American Chemical Society, Jan. 27, 2005, vol. 127, No. 7, pp. 2264-2271 (8 pgs).
Hall et al., "Antioxidant Therapies for Traumatic Brain Injury," Neurotherapeutics: The Journal of the American Society for Experimental NeuroTherapeutics, vol. 7, Jan. 2010, pp. 51-61 (11 pgs).

Hellerstein et al., "A critique of the molecular target-based drug discovery paradigm based on principles of metabolic control: Advantages of pathway-based discovery," Metabolic Engineering, vol. 10, pp. 1-9, 2008 (9 pgs).
Hwang et al., Indole-3-propionic acid attenuates neuronal damage and oxidative stress in the ischemic hippocampus. J Neurosci Res. Jul. 2009;87(9):2126-37. doi: 10.1002/jnr.22030. PMID: 19235887 [PubMed—indexed for MEDLINE] (12 pgs).
International Preliminary Report on Patentability issued in application No. PCT/US2014/045139, dated Jan. 14, 2016 (9 pgs).
International Preliminary Report on Patentability issued in application No. PCT/US2015/013888, dated Aug. 11, 2016 (9 pgs).
International Search Report and Written Opinion issued in application PCT/US15/13888, dated Jul. 24, 2015 (12 pgs).
International Search Report and Written Opinion issued in corresponding application No. PCT/US2013/033918, dated Jun. 14, 2013 (15 pgs).
International Search Report and Written Opinion issued in related application No. PCT/US14/45139, dated Nov. 10, 2014 (10 pgs).
James et al., "Pharmacokinetics of Acetaminophen-Protein Adducts in Adults with Acetaminophen Overdose, and Acute Liver Failure," Drug Metabolism and Disposition, vol. 37, No. 8, May 13, 2009, pp. 1779-1784 (6 pgs).
Japanese Decision of Refusal (w/translation) issued in application No. 2016-524329, dated Jun. 20, 2019 (15 pgs).
Japanese Office Action (w/translation) issued in application No. 2016-524329, dated Feb. 22, 2018 (9 pgs).
Japanese Office Action (w/translation) issued in application No. 2016-524329, dated Oct. 16, 2018 (11 pgs).
Japanese Office Action (w/translation) issued in application No. 2016-549363, dated Dec. 28, 2018 (11 pgs).
Japanese Office Action (w/translation) issued in application No. 2016-549363, dated Sep. 25, 2019 (9 pgs).
Japanese Office Action (w/translation) issued in application No. 2016-549363, dated Jun. 1, 2020 (6 pgs).
Japanese Trial Decision of Refusal (translation) issued in Appeal No. 2019-014089, dated Jul. 7, 2020 (56 pgs).
Johansen, et al., "Metabolomic Profiling in LRRK2-Related Parkinson's Disease," PLoS ONE. Oct. 2009; 4(10): e7551 (9 pgs).
Kaddurah-Daouk et al., "Metabolomic changes in autopsy confirmed Alzheimer's disease," Alzheimers Dement. May 2011; 7(3): 309-317 (14 pgs).
Kaddurah-Daouk et al., "Pretreatment metabotype as a predictor of response to sertraline or placebo in depressed outpatients: a proof of concept," Transl Psychiatry. Jul. 26, 2011; 1(7): e26 (7 pgs).
Karbownik et al., "Carcinogen-induced, free radical-mediated reduction in microsomal membrane fluidity: reversal by indole-3-propionic acid," J Bioenerg Biomembr. Feb. 2001;33(1):73-8. PMID: 11460928 [PubMed—indexed for MEDLINE] (6 pgs).
Karbownik et al., "Comparison of potential protective effects of melatonin, indole-3-propionic acid, and propylthiouracil against lipid peroxidation caused by potassium bromate in the thyroid gland," J Cell Biochem. May 1, 2005;95(1):131-8. PMID: 15723291 [PubMed—indexed for MEDLINE] (8 pgs).
Karsdal et al., "Novel combinations of Post-translational Modification (PTM) neo-epitopes provide tissue-specific biochemical markers—are they the cause or the consequence of the disease?", Clinical Biochemistry, vol. 43, No. 10-11, pp. 793-804 (abstract only, 2 pgs).
Kato et al., "Analytical method for β-amyloid fibrils using CE-laser induced fluorescence and its application to screening for inhibitors of β-amyloid protein aggregation," Anal Chem. Jul. 1, 2007;79(13):4887-91. Epub May 31, 2007 (5 pgs).
Langen et al. (Inflamm Bowel Dis., 2009; 15(3):454-462) (Year: 2009) (21 pgs).
LeWitt et al., "Markers of dopamine metabolism in Parkinson's disease," The Parkinson Study Group. Neurology, Nov. 1992;42(11):2111-7 (7 pgs).
Lopez-Otin et al., The Hallmarks of Aging, Cell, 2013, 153, 1194-1217 (24 pgs).
M. Nic, J. Jirat, B. Kosata, "coordination" Aug. 19, 2012. IUPAC. Compendium of Chemical Terminology, $2^{nd}$ ed. (the Gold Book).

(56) References Cited

OTHER PUBLICATIONS

Compiled by A. D. McNaught and A. Wilkinson. Blackwell Scientific Publications, Oxford, 1997, updates compiled by A. Jenkins (2 pgs).
M. Nic, J. Jirat, B. Kosata, "covalent bond" Aug. 19, 2012. IUPAC. Compendium of Chemical Terminology, $2^{nd}$ ed. (the Gold Book). Compiled by A. D. McNaught and A. Wilkinson. Blackwell Scientific Publications, Oxford, 1997, updates compiled by A. Jenkins (2 pgs).
Mattson, M., "Excitotoxic and Excitoprotective Mechanisms," NeuroMolecular Medicine, vol. 3, 2003, pp. 65-94 (30 pgs).
Mellick et al., "Exploiting the potential of molecular profiling in Parkinson's disease: current practice and future probabilities," Expert Review of Molecular Diagnostics, vol. 10, No. 8, Nov. 1, 2010, pp. 1035-1050 (16 pgs).
Nam et al., "Melatonin protects against neuronal damage induced by 3-nitropropionic acid in rat striatum," Brain Research. 2005: 90-96 (7 pgs).
Notice of Allowance issued in U.S. Appl. No. 14/688,781, dated Mar. 13, 2017 (16 pgs).
Notice of Allowance issued in U.S. Appl. No. 13/829,773, dated Apr. 19, 2017 (16 pgs).
Notice of Allowance issued in U.S. Appl. No. 14/092,677, dated Nov. 8, 2016 (18 pgs).
Notice of Allowance issued in U.S. Appl. No. 14/688,781, dated Dec. 8, 2016 (23 pgs).
Office Action issued in U.S. Appl. No. 13/829,773, dated Nov. 3, 2016 (24 pgs).
Office Action issued in U.S. Appl. No. 13/829,773, dated Feb. 8, 2016 (16 pgs).
Office Action issued in U.S. Appl. No. 13/829,773, dated Jun. 22, 2016 (22 pgs).
Office Action issued in U.S. Appl. No. 13/829,773, dated Sep. 11, 2015 (14 pgs).
Office Action issued in U.S. Appl. No. 14/092,677, dated Apr. 14, 2016 (33 pgs).
Office Action issued in U.S. Appl. No. 14/092,677, dated Aug. 1, 2016 (26 pgs).
Office Action issued in U.S. Appl. No. 14/092,677, dated Dec. 10, 2015 (13 pgs).
Office Action issued in U.S. Appl. No. 14/092,677, dated Jul. 23, 2015 (17 pgs).
Office Action issued in U.S. Appl. No. 14/092,677, dated Sep. 11, 2015 (12 pgs).
Office Action issued in U.S. Appl. No. 14/321,569, dated Feb. 14, 2019 (19 pgs).
Office Action issued in U.S. Appl. No. 14/321,569, dated Jan. 26, 2016 (21 pgs).
Office Action issued in U.S. Appl. No. 14/321,569, dated Jan. 23, 2017 (17 pgs).
Office Action issued in U.S. Appl. No. 14/321,569, dated Jul. 20, 2015 (38 pgs).
Office Action issued in U.S. Appl. No. 14/321,569, dated Jul. 27, 2016 (23 pgs).
Office Action issued in U.S. Appl. No. 14/321,569, dated Jun. 6, 2016 (21 pgs).
Office Action issued in U.S. Appl. No. 14/321,569, dated Nov. 15, 2018 (25 pgs).
Office Action issued in U.S. Appl. No. 14/321,569, dated Sep. 18, 2015 (21 pgs).
Office Action issued in U.S. Appl. No. 14/515,399, dated Jan. 25, 2017 (24 pgs).
Office Action issued in U.S. Appl. No. 14/515,399, dated Jun. 22, 2016 (14 pgs).
Office Action issued in U.S. Appl. No. 14/515,399, dated Mar. 1, 2016 (19 pgs).
Office Action issued in U.S. Appl. No. 14/515,399, dated Sep. 8, 2015 (23 pgs).
Office Action issued in U.S. Appl. No. 14/610,779, dated Dec. 22, 2015 (48 pgs).
Office Action issued in U.S. Appl. No. 14/610,779, dated Jun. 14, 2016 (33 pgs).
Office Action issued in U.S. Appl. No. 14/610,779, dated Oct. 9, 2015 (20 pgs).
Office Action issued in U.S. Appl. No. 14/688,781, dated Feb. 11, 2016 (25 pgs).
Office Action issued in U.S. Appl. No. 14/688,781, dated Jun. 7, 2016 (19 pgs).
Office Action issued in U.S. Appl. No. 14/688,781, dated Sep. 10, 2015 (29 pgs).
Office Action issued in U.S. Appl. No. 14/688,781, dated Sep. 20, 2016 (22 pgs).
Office Action issued in U.S. Appl. No. 14/828,204, dated Apr. 22, 2016 (36 pgs).
Office Action issued in U.S. Appl. No. 14/828,204, dated Apr. 27, 2017 (18 pgs).
Office Action issued in U.S. Appl. No. 14/828,204, dated Aug. 4, 2017 (17 pgs).
Office Action issued in U.S. Appl. No. 14/828,204, dated Jul. 28, 2016 (24 pgs).
Office Action issued in U.S. Appl. No. 14/828,204, dated Mar. 9, 2017 (17 pgs).
Office Action issued in U.S. Appl. No. 14/828,204, dated May 21, 2018 (16 pgs).
Office Action issued in U.S. Appl. No. 14/828,204, dated Nov. 16, 2016 (16 pgs).
Office Action issued in U.S. Appl. No. 14/828,204, dated Nov. 9, 2017 (5 pgs).
Office Action issued in U.S. Appl. No. 14/828,211, dated Aug. 11, 2016 (17 pgs).
Office Action issued in U.S. Appl. No. 14/828,211, dated Feb. 5, 2018 (19 pgs).
Office Action issued in U.S. Appl. No. 14/828,211, dated Jul. 11, 2017 (16 pgs).
Office Action issued in U.S. Appl. No. 14/828,211, dated Mar. 20, 2017 (17 pgs).
Office Action issued in U.S. Appl. No. 14/828,211, dated May 18, 2018 (24 pgs).
Office Action issued in U.S. Appl. No. 14/828,211, dated May 19, 2016 (36 pgs).
Office Action issued in U.S. Appl. No. 14/828,211, dated May 24, 2017 (8 pgs).
Office Action issued in U.S. Appl. No. 14/828,211, dated May 5, 2016 (6 pgs).
Office Action issued in U.S. Appl. No. 14/828,211, dated Nov. 25, 2016 (14 pgs).
Office Action issued in U.S. Appl. No. 14/828,211, dated Oct. 25, 2017 (16 pgs).
Office Action issued in U.S. Appl. No. 15/277,861, dated Apr. 25, 2017 (43 pgs).
Office Action issued in U.S. Appl. No. 15/277,861, dated Apr. 8, 2019 (48 pgs).
Office Action issued in U.S. Appl. No. 15/277,861, dated Aug. 29, 2018 (49 pgs).
Office Action issued in U.S. Appl. No. 15/277,861, dated Feb. 15, 2018 (46 pgs).
Office Action issued in U.S. Appl. No. 15/277,861, dated Nov. 9, 2018 (42 pgs).
Office Action issued in U.S. Appl. No. 15/277,861, dated Oct. 24, 2017 (32 pgs).
Office Action issued in U.S. Appl. No. 15/724,053, dated Aug. 13, 2018 (12 pgs).
Office Action issued in U.S. Appl. No. 15/724,053, dated Dec. 1, 2017 (20 pgs).
Office Action issued in U.S. Appl. No. 15/724,053, dated Jun. 15 2018 (17 pgs).
Office Action issued in U.S. Appl. No. 15/724,053, dated Mar. 9, 2018 (15 pgs).
Office Action issued in U.S. Appl. No. 15/724,053, dated Sep. 27, 2018 (23 pgs).
Office Action issued in U.S. Appl. No. 16/258,199, dated Dec. 26, 2019 (14 pgs).

(56) References Cited

OTHER PUBLICATIONS

Office Action issued in U.S. Appl. No. 16/258,199, dated Aug. 16, 2019 (18 pgs).
Office Action issued in U.S. Appl. No. 16/258,199, dated May 10, 2019 (32 pgs).
Office Action issued in U.S. Appl. No. 16/258,199, dated Nov. 6, 2019 (14 pgs).
Office Action issued in related U.S. Appl. No. 13/829,773, dated Aug. 20, 2014 (33 pgs).
Office Action issued in related U.S. Appl. No. 13/829,773, dated Mar. 6, 2015 (25 pgs).
Office Action issued in related U.S. Appl. No. 14/092,677, dated Mar. 27, 2015 (26 pgs).
Office Action issued in related U.S. Appl. No. 14/515,399, dated Apr. 2, 2015 (31 pgs).
Pauley et al., "Effect of Tryptophan Analogs on Derepression of the *Escherichia coli* Tryptophan Operon by Indole-3-Propionic Acid," Journal of Bacteriology, Oct. 1978, vol. 136, No. 1, pp. 219-226 (8 pgs).
Poeggeler et al., "Indole-3-propionate: a potent hydroxyl radical scavenger in rat brain", Brain Research, Elsevier, 815 (1990) 382-388 (7 pgs).
Preliminary Report on Patentability; Appln. No. PCT/US2013/033918, dated Oct. 1, 2014, (12 pgs).
Rahman, K., Studies on free radicals, antioxidants, and co-factors, Clinical Interventions in Aging, 2007 2(2), 219-236 (18 pgs).
Richardot et al., "Nitrated type III collagen as a biological marker of nitric oxide-mediated synovial tissue metabolism in osteoarthritis," Osteoarthritis and Cartilage, vol. 17, No. 10, Oct. 1, 2009, pp. 1362-1367 (6 pgs).
Rosas et al., "A systems-level "misunderstanding": the plasma metalolome in Huntington's disease", Annals of Clinical and Translational Neurology, Open Access, dated Apr. 11, 2015, pp. 756-768 (13 pgs).
Rozen et al., "Metabolomic analysis and signatures in motor neuron disease," Metabolomics. 2005; 1(2): 101-108 (14 pgs).
Schiavo et al., "Metabolite Identification Using a Nanoelectrospray LC-EC-array-MS Integrated System," Anal Chem. Aug. 1, 2008; 80(15): 5912-5923 (21 pgs).
Signoretti et al., PMR 2011; 3: S359-368 (10 pgs).
Sitorius, E., "Development of Fourier Transform Mid-Infrared Spectroscopy as a Metabolomic Technique for Characterizing the Protective Properties of Grain Sorghum Against Oxidation," May 1, 2010, Dissertations & Theses in Food Science and Technology, Digital Commons at the University of Nebraska, Lincoln (94 pgs).
Smith et al., "Formation of Phenolic and Indolic Compounds by Anaerobic Bacteria in the Human Large Intestine," Microbial Ecology, vol. 33, No. 3, Apr. 1997, pp. 180-188 (9 pgs).
Swinney et al., "How were new medicines discovered?" Nature Reviews, vol. 10, pp. 507-519, 2011 (13 pgs).
Tandara et al., "Iron metabolism: current facts and future decisions," 2012, Biochemica Medica, vol. 22, issue 3, pp. 311-328 (14 pgs).
Thomas et al., "A novel method for detecting 7-methyl guanine reveals aberrant methylation levels in Huntington disease", Anal Biochem, May 15, 2013;436(2):112-20. doi: 10.1016/j.ab.2013.01.035. Epub Feb. 12, 2013 (19 pgs).
Valko et al., Free radicals, metals and antioxidants in oxidative stress-induced cancer, Chemico-Biological Interactions, 2006, 160, 1-40 (40 pgs).
Vickers, J.C., A Vaccine Against Alzheimer's Disease, Drugs Aging, 2002, 19(7): 487-494 (8 pgs).
Waldmeier et al., "Absorption, Distribution, Metabolism, and Elimination of the Direct Renin Inhibitor Aliskiren in Health Volunteers," 2007; 35: 1418-1428 (11 pgs).
Weimann et al., "Assays for urinary biomarkers of oxidatively damaged nucleic acids," Free Radical Research, vol. 46, No. 4, Apr. 2012, pp. 531-540 (11 pgs).
Wikoff et al., "Metabolomics analysis reveals large effects of gut microflora on mammalian blood metabolites," PNAS. Mar. 10, 2009; 106(10): 3698-3703 (6 pgs).
Williams et al., "Serum Metabolic Profiling in Inflammatory Bowel Disease," Dig Dis Sci, Apr. 10, 2012, vol. 57, pp. 2157-2165 (9 pgs).
Wolff et al., "Epigenetic repression of regulator of G-protein signaling 2 promotes androgen-independent prostate cancer cell growth," Internal Journal of Cancer, vol. 130, No. 7, Jun. 2011, pp. 1521-1531 (16 pgs).
Yang et al., "Effects of High Tryptophan Doses and Two Experimental Rations on the Excretion of Urinary Tryptophan Metabolites in Cattle" *The Journal of Nutrition*, 102: 1655-1666, 1972 (11 pgs).
Yara et al., Iron-Ascorbate-Mediated Lipid Peroxidation Causes Epigenetic Changes in the Antioxidant Defense in Intestinal Epithelial Cells: Impact on Inflammation, PLOS One, 2013, (8(5), 1-11 (11 pgs).
Yoshida et al., "Direct Enrichment of Tryptophan and Its Metabolites in Plasma onto a Pre-column Followed by Reverse Phase HPLC Analysis," Chem Pharm Bull, 1982; 30: 3827-3830 (4 pgs).
Yu et al. World J Gastroenterol Feb. 28, 2018; 24(8): 894-904) (Year: 2018) (15 pgs).

\* cited by examiner

```
┌─────────────────────────────────┐
│ Solubilize a dried sample to yield a │
│       solubilized sample        │
│              202                │
└─────────────────────────────────┘
                 ↓
┌─────────────────────────────────┐
│ Optionally process the solubilized │
│             sample              │
│              204                │
└─────────────────────────────────┘
                 ↓
┌─────────────────────────────────┐
│  Measure metabolites of interest │
│ present in the solubilized sample│
│              206                │
└─────────────────────────────────┘
                 ↓
┌─────────────────────────────────┐
│ Determine health/disease state based│
│  on the measured metabolites of │
│            interest             │
│              208                │
└─────────────────────────────────┘
                 ↓
┌─────────────────────────────────┐
│ Provide recommendations based on │
│    the health/disease state     │
│              210                │
└─────────────────────────────────┘
                 ↓
┌─────────────────────────────────┐
│ Periodically collect and remeasure│
│ metabolites of interest, determine│
│ health/disease state, and provide │
│ revised recommendations based on │
│    the health/disease state     │
│              212                │
└─────────────────────────────────┘
```

FIG. 2

| Metabolite | Ideal Range | Health Categories |
| --- | --- | --- |
| Indole Propionic Acid (IPA) | >55 ng/ml | GI, IF, CA, |
| Indole-3-Lactic Acid (ILA) | 50-500 ng/ml | GI |
| Indole-3-Acetic Acid (IAA) | 30-300 ng/ml | GI |
| Tryptophan (TRP) | 4.1-9.5 ug/ml | GI, IF, EB, CA, EE |
| Serotonin (SER) | 15-120 ng/ml | GI, IF, EB, CA |
| Kynurenine (KYN) | 75-350 ng/ml | IF, EB CA, EE |
| Total Indoxyl Sulfate (IDS) | <400 ng/ml | IF |
| Tyrosine (TYR) | 4.5-20.5 ug/ml | GI, IF CA, EE |
| Xanthine (XAN) | 30-190 ng/ml | EE |
| 3-Methylxanthine (3MXAN) | <500 ng/ml | GI, EB |
| Uric Acid (UA) | 15-42 ug/ml Men<br>11.1-36 ug/ml Women | GI, IF, EE |

Health Categories:
Gastrointestinal Fitness (GI), Immuno-Fitness (IF), Emotional Balance (EB), Cognitive Acuity (CA), Energetic Efficiency (EE)

DETECTION AND MODIFICATION OF GUT MICROBIAL POPULATION

CROSS REFERENCE

This application is a continuation-in-part (CIP) application of my co-pending U.S. application Ser. No. 16/258,199, filed Jan. 25, 2019, the contents of which are incorporated herein by reference.

FIELD

The present disclosure relates generally to systems and methods for evaluating health or disease state of an individual, and for improving the health of the individual. In particular, the disclosed systems and methods measure the levels of one or more metabolites of interest in the individual to determine a current state of the gut microbial population of an individual, and provide a personalized program for improving the health of the individual. Specifically, the present disclosure identifies and describes techniques for measuring levels of certain key metabolites, and using the measured metabolite levels to assess heath state/disease state or disease risk of the individual. The present disclosure also describes methods for providing behavior modification, e.g., relating to nutrition, physical training, sleep, or mental wellness, and for providing supplements, to improve health, disease state, or disease risk of an individual, based on the measured metabolite levels of the individual.

SUMMARY

The gut is colonized by many (6-10,000) different species of bacteria, viruses, parasites, fungus and archaea. Diversity of the gut microbiome is dependent on many factors, e.g., genetics, illness, diet, and drug use, and thus there is large individual variation of the population in the gut. At times, there exists a need to evaluate an individual's microbiome. Many microbiome tests employ stool samples and only measure certain species of bacteria or other microorganisms present in the stool sample. While stool sample tests often can identify the presence of some bacteria, stool sample tests are difficult to collect and only reveal the existence of a limited number and species of bacteria, etc., present in the gut. As such, stool sample tests cannot provide guidance regarding overall health, disease state or disease risk of an individual, or recommend actions for improving health disease state or disease risk.

Other factors also must be considered. First all of the species in the gut are essentially in a Darwinian competition for survival dominance and activity. This essentially means that the mere existence of a species in the stool does not necessarily indicate its activity in either utilizing or producing compound that leaves the gut to carry out functions in the rest of the body. Second the functionality of the gut microbiome is affected not only by environmental behavioral factors (diet, stress, exercise etc.) but by the underlying genome of the individual. As will be discussed below, we have shown this in studies of the small molecule footprint in feces by which young just weaned gene modified and wild type littermate mice could be uniquely discriminated from each other. Same cage-same mother-same microbiome-same environmental exposures different gut functionality.

Thus measuring the result of microbiome activity as it affects levels of microbiome modified compounds in the plasma, whole blood, or DBS allows direct understanding of the role of the microbiome. This provides a set of essential materials for monitoring and optimizing health and risk through control/modification of the microbiome functionality. Embodiments of the present disclosure provide methods and systems for indirect measuring levels of certain key metabolites of the gut microbiome that effect system health of an individual and take into account the effect of different microbial species as well as the important metabolic pathways influenced by the gut microbiome, by measuring certain microbiome modified compounds in a blood sample of an individual. More particularly, we have found that certain key metabolites of the gut microbiome which can be indirectly measured through the presence of certain microbiome modified compounds in a blood sample, play an outsized role in effecting many aspects of health of an individual, including gut health, emotional balance, cognitive acuity, energetic efficiency and immuno fitness, and can easily be adjusted to improve the health state of the individual. These particular key metabolites are indole propionic acid (IPA), indole-3-lactic acid (ILA), indole-3-acetic acid (IAA), Tryptophan (TRP), Serotonin (SER), Kynurenine (KYN), Total Indoxyl Sulfate (IDS), Tyrosine (TYR), Xanthine (XAN), 3-Methylxanthine (3MXAN), and Uric Acid (UA).

In one aspect the present disclosure provides a method for improving the health or disease state of an individual, by indirectly measuring the concentration of certain key metabolites of the gut comprising collecting liquid samples from the body of said individual and analyzing said liquid samples for concentration of two or more of the following microbiome modified compounds selected from the group consisting of: indole propionic acid (IPA), indole-3-lactic acid (ILA), indole-3-acetic acid (IAA), Tryptophan (TRP), Serotonin (SER), Kynurenine (KYN), Total Indoxyl Sulfate (IDS), Tyrosine (TYR), Xanthine (XAN), 3-Methylxanthine (3MXAN), and Uric Acid (UA); comparing the concentration of said selected microbiome modified compounds to standards; and, prescribing a treatment protocol to raise or reduce the concentration, as the case may be, for those metabolites that fall outside of an accepted range.

In one embodiment, the liquid sample preferably comprises blood, although urine, saliva or tears also could be tested.

In another embodiment, a minimum of three, four, five, six, seven, eight, nine, ten, eleven or twelve of said metabolites are analyzed.

In another embodiment, the treatment protocol includes administration of one or more supplements selected from the group consisting of a prebiotic, a probiotic, melatonin, a vitamin B complex, copper, and CoQ10.

The microbiome modified compounds are described below.

Indole Propionic Acid (IPA) is produced in the human gut exclusively by one species of gut bacteria (*Clostridium sporogenes*) from tryptophan. Research indicates that if dysbiosis is occurring, these are amongst the first bacteria to be negatively impacted, resulting in lower IPA levels. Thus, IPA is a critical marker for a healthy gut microbiome. IPA is also considered to be one of the strongest antioxidants in the body. Oxidative stress is a damaging process that results in tissue damage and cell death and IPA has been shown to protect cells from oxidative stress damage, which plays an important role in a variety of systems health including brain health. Additionally, IPA plays a crucial role in maintaining a healthy gut by strengthening the tight junctions (spaces) between the cells lining the gut. This is important for maintaining intestinal structural integrity and decreasing intestinal permeability. Intestinal permeability can lead to substances exiting the intestine into the bloodstream leading to conditions such as food allergies.

Indole-3-Lactic Acid (ILA) is a tryptophan metabolite and precursor to indole-3-propionic acid (IPA) and is important for strong internal fitness. Low levels of ILA may prevent the formation of adequate amounts of downstream metabolites such as indole-3-propionic acid (IPA). Low levels of ILA may also indicate low levels of *Bifidobacterium* in the intestine. *Bifidobacterium* can assist with conversion of tryptophan to ILA and low levels of *Bifidobacterium* can lead to further dysbiosis. However, high levels of ILA may also lead to gut dysfunction and discomfort because, at high levels, ILA can be toxic to the beneficial bacteria in the microbiome. Excessive high levels of ILA may also indicate dysbiosis of the gut metabolome, because the bacterium *Clostridium sporogenes* that uses ILA to make indole-3-propionic acid (IPA) may be too low to effectively convert ILA to IPA. If the quantity of beneficial bacteria decreases significantly, there is a chance that invasive bacterial species can proliferate, leading to further dysbiosis.

Indole-3-Acetic Acid (IAA) is an indirect precursor to IPA and is also an auxin produced in plants. IAA has been shown to possess antioxidant activity and low levels of indole-3-acetic acid (IAA) are generally not a problem. However, low IAA should be considered in the context of other metabolites in the tryptophan branch, specifically indole-3-propionic acid (IPA). If both IAA and IPA are low, this can be a marker of gut dysbiosis. High levels of IAA have been reported to inhibit the growth and survival of the beneficial *Lactobacillus* species of gut bacteria, which converts sugars such as glucose and fructose to lactic acid, which may inhibit the growth of some harmful bacteria. High levels of IAA also have been associates with poor kidney and heart health.

Tryptophan (TRP) is obtained mainly through one's diet. Certain gut bacteria are also capable of making tryptophan. Tryptophan is an amino acid. Amino acids are building blocks for proteins that are essential for maintaining a healthy body. Some of these proteins include antibodies (for immunity), hormones (for signaling), muscles (for movement), and enzymes (for biochemical reactions). Tryptophan can cross the blood-brain barrier, making it available to produce important neurotransmitters like serotonin, which is essential for normal brain processes that affect mood, behavior, memory, and learning. Many digestive disorders can change tryptophan levels. Factors like stress, gut dysbiosis, and infection enhance tryptophan degradation, resulting in lower tryptophan levels. Low tryptophan levels have been associated with gut dysbiosis and "fad dieting" and have also been linked to occasional difficulties sleeping and muscle aches and pains. High levels of tryptophan may also be the result of gut dysbiosis. In some such cases, the gut microbiome may not be breaking down the tryptophan efficiently to create other necessary metabolites. Higher levels of tryptophan have been observed after major surgeries and in subjects with high protein diets. High levels of tryptophan have been linked to mood swings, increased aggressiveness, and tremors.

Serotonin (SER) is a tryptophan metabolite. Serotonin synthesis is facilitated by the adequate presence of vitamins B1, B3, B6, and folic acid. Serotonin is one of the most important signaling molecules within the gut, where it plays a pivotal role in initiating secretions (mucosal) and motor reflexes (the movement of the intestine) and is crucial for normal functionality of the central nervous system. Most of the body's serotonin is produced by cells in the intestinal wall. Approximately 95% of circulating serotonin originates from these cells. Gut dysbiosis or an inflammation of the gut may interfere with the enterochromaffin cells that make serotonin in the intestinal lining. Low levels of serotonin have been linked to occasional sleep problems, muscle aches and pains, poor brain health, and poor gut health. High levels of serotonin can be linked to shivering, diarrhea, and muscle tightness. Additionally, high levels of serotonin have also been linked to occasional agitation, restlessness, confusion, poor heart health, dilated pupils, muscle aches and pains, sweating, headaches, and goose bumps.

Kynurenine (KYN) is a metabolite of tryptophan. Its primary function is to dilate blood vessels during an inflammatory response. Kynurenine is also a regulator of the immune system. Kynurenine is used in the production of niacin (vitamin B3). Niacin is considered to be one of the essential human nutrients as it participates in DNA repair. Kynurenine is utilized by the endocrine system to produce certain hormones. Kynurenic acid, a metabolite of kynurenine, is a neuroprotective agent in the brain. Its production is mediated by vitamin B6, selenium, and sulfur containing amino acids. Kynurenine also acts in the eye to protect against UV radiation. Low levels of kynurenine may be caused by gut imbalances and low levels of kynurenine can lead to low levels of downstream metabolites (kynurenic acid) and vitamin B3. Low levels of kynurenine have also been linked to decreased energy and gut dysbiosis. The most common cause of elevated kynurenine and its metabolites is the excessive use of tryptophan supplementation. Additional causes include the presence of chronic infections and vitamin B6 deficiency. Changes in the ratio of kynurenine to tryptophan are an indication of a general health imbalance. Exercise can be a key modulator of kynurenine because it reduces kynurenine levels and thus reduces excretion of its downstream metabolic product, kynurenic acid.

Total Indoxyl Sulfate (IDS) is a metabolite of tryptophan and is absorbed into the blood from the liver. IDS is a toxin made from a gut bacteria metabolite in the liver and is a molecule known as a uremic toxin. High levels of IDS has been associated with poor kidney and heart health. Low levels of indoxyl sulfate (IDS) are considered positive. Research suggests that normal levels of indoxyl sulfate may act as an antioxidant and high levels of IDS can lead to oxidative stress in numerous cell types, including vascular smooth muscle cells, endothelial cells, and bone cells. High levels have also been found in people who take too much tryptophan supplement.

Tyrosine (TYR) is a nonessential amino acid, which means that an individual can synthesize it from another amino acid, phenylalanine. Tyrosine is present in almost every protein in the body. Tyrosine functions as a building block for several important neurotransmitters, such as dopamine, epinephrine, and norepinephrine. Neurotransmitters regulate mood, behavior, and general feelings of well-being. Tyrosine is needed for the thyroid gland to produce hormones T3 and T4 (which regulate growth, metabolism, body temperature, and heart rate). Tyrosine is also an important amino acid for the pituitary gland. The pituitary gland, like the thyroid gland, controls metabolism and growth; additionally, it regulates sexual maturation, reproduction, blood pressure, and many other vital physical processes. Tyrosine is also necessary for cell division. Low levels of tyrosine are rare; however, some researchers believe that stress may affect the body's ability to make tyrosine. Low levels of tyrosine can lead to poor brain health and abnormally high levels of tyrosine can lead to poor gut and brain health and have also been linked to anxiety. High protein diets can raise tyrosine levels. High levels of Tyrosine may also be the result of a gut dysbiosis when, for example, the body's gut microbiome is not breaking down the tyrosine efficiently into other metabolites. High levels of tyrosine are also associated with a genetic disorder called tyrosinemia. This condition is caused by the deficiency of one of the enzymes required for the multistep process that breaks down tyrosine.

Xanthine (XAN) is a metabolite of the purine pathway and functions in the digestive tract to induce hydrochloric acid production and promote secretion of pepsin from cells lining the stomach. Both of these processes help to break down consumed food. Xanthine is also a mild stimulant and is found in coffee, cola, and green tea. Very low levels of xanthine are rarely seen except in cases of a genetic disorder called xanthinuria. Low levels of xanthine can lead to digestive discomfort due to the role xanthine plays in inducing digestive enzymes. Xanthine levels at the low end of normal can be associated with oxidative stress. High levels of xanthine can be caused by overconsumption of caffeinated beverages and by certain medications (bronchodilators), as well as high purine diets. High levels of xanthine have been linked to nausea, elevated heart rate, and poor heart health.

3-Methylxanthine (3MXAN) is a purine metabolism-breakdown product in caffeine and theophylline. Metabolites of the purine pathway are significant because they affect both the gut and the brain. In the gut, 3MXAN increases hydrochloric acid and pepsin secretion, which aid in digestion. Purines are key components of cellular energy systems (e.g., ATP and NAD), cellular signaling, and along with pyrimidines are involved in RNA and DNA production. Presently there is limited research to indicate physiological effects when low levels of 3-methylxanthine (3MXAN) are present. However, because methylxanthines increase hydrochloric acid and pepsin secretion in the GI tract, slow digestion might be aided by consuming a cup of tea with or after a meal. High levels of 3MXAN can be an indication of medication used for chronic obstructive pulmonary disease (COPD) and asthma or of excessive intake of caffeine products. Individuals suffering from acid reflux are encouraged to limit their intake of methylxanthines. It is thought that a high-carbohydrate/low-protein diet can decrease the removal of 3MXAN from the blood at a normal rate, accordingly, a diet high in fiber and protein may reduce 3MXAN levels.

Uric Acid (UA) is the final product of human purine metabolism. Uric acid may be a marker of oxidative stress. Approximately ⅓ of purines are derived from diet. The majority of uric acid is dissolved in the blood, filtered through the kidneys, and expelled in the urine. Low levels of uric acid may be an indication of over hydration or a low-purine diet. High levels of uric acid can be hereditary or could be a symptom of gout. High levels can also be caused by temporary dehydration, excessive beer drinking, and/or a high-purine diet. It has been reported that fructose intolerance can be indicated by high levels of uric acid.

4-Hydroxybenzoic Acid (4HBAC) is believed to also be a key metabolite of the gut microbiome. However, 4HBAC is somewhat unstable and cannot be reliably measured. Notwithstanding, 4HBAC also is included as a metabolite of interest, as discussed below. 4HBAC is found naturally in lentils, vanilla, gooseberries, and mushrooms. 4-Hydroxybenzoic Acid has also been found in humans after drinking green tea and wine. 4HBAC is a popular antioxidant because of its low toxicity. 4HBAC and its precursor benzoic acid are produced by bacteria in the gut and can be used as an indicator of intestinal dysbiosis or leaky gut syndrome. Esters of 4HBAC are referred to as parabens and are used widely as antimicrobial preservatives in cosmetics, for pharmaceutical applications, and in processed foods. Low levels of 4-hydroxybenzoic acid (4HBAC) do not appear to have any adverse physiological effects; however, low levels may be an indication that ingested natural antioxidants are in low quantity. Abnormally high levels of 4HBAC can lead to intestinal dysbiosis and can also be an indication of increased intestinal permeability ("leaky gut"). Exposure to high concentrations of processed foods or skin creams with parabens can increase levels of 4HBAC. Parabens functionally mimic estrogens and have been associated with low energy and poor skin health. Overindulgence in fruits such as blueberries can increase the levels of 4HBAC.

In practice for dietary recommendations these micrbobiome modified molecules are not considered singly but as an entire network. In the simplest form this is as ratios of each compound to all other compounds (I. E. 78 separate variables). As an example KYN to TRP is a ratio that in the normal population has a relative standard deviation of approximately 30% with a within individual variation from several samples of approximately 10%. However, concussion will elevate this ratio as well certain types of cancers and other diseases. Normal levels are related to gut functionality. Similarly low IPA, high UA, and IAA individually constitute risk factors for cardiovascular disease. Considered together they modify the assessment of risk in evaluation of mediation strategies. In a more complex data treatment, given a larger number of samples and outcomes, the data can be organized using grouping of profiles versus outcome techniques such as PCA (unsupervised principal component analysis) or PLSDA (partial least squares discriminate analysis) using Umetrics Simca-P software available from Sartorius Stedim Biotech and Matlab software available from MathWorks, Inc., or correlation networks could be used as taught in prior U.S. Pat. No. 6,194,217, the context of which are incorporated herein by reference.

In contrast with previous techniques of evaluating the gut microbiome through stool sampling, the presently disclosed systems and methods are able to indirectly measure key metabolites of the gut by measuring the functional effect of how the gut microbiome is working (the output of the organisms in the gut) and how these organisms interact with the gut to put necessary nutrients and occasionally undesirable compounds into the blood. Only knowing what is in the gut microbiome does not provide information regarding how the gut is functioning to provide biochemicals that run and control the body. Thus, a stool sample alone provides an incomplete picture of an individual's health/disease state.

Molecules called short chain fatty acids (SCFAs) are created by bacteria in the gut during the fermentation process from carbohydrates and proteins. SCFAs have several effects in the body including epithelial cell transport and metabolism. SCFAs also provide energy sources for muscles and kidneys, as well as for the heart and brain. Because 95% of metabolites created by SCFAs are absorbed from the gut, fecal analysis of SCFAs and their metabolites is not particularly useful in healthy people. On the other hand, being able to measure the "output" of SCFAs can provide insight into whether the gut is functioning properly.

In some aspects, the disclosed techniques allow correlations between various functions of the body to be observed (for example, correlations between exercise and the gut microbiome). The disclosed systems and methods may also, in some embodiments, measure the output of bacteria present in the microbiome, which indicates whether specific compounds in the body are where they need to be and may allow an individual to use this information to make alterations to improve their metabolite levels.

In various embodiments, a blood sample from an individual is used to evaluate output from bacteria in the microbiome. It has been found that blood samples can capture a significant part of the complexity of microbiome interactions. The results from measuring some critical nutritional, energetic, control, and protective markers present in a blood sample can be used to modify and monitor parameters that reflect suboptimal function. Based on the profile of the metabolites measured in a blood sample, one or more recommendations can be made from a detailed meta-analysis of available peer reviewed literature, internal data and studies, and general best practice in nutrition, training, and supplementation.

The features, functions, and advantages that have been discussed can be achieved independently in various embodiments of the present disclosure or may be combined in yet other embodiments, further details of which can be seen with reference to the following description and drawings. Other features, functions and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure.

Moreover, in the drawings, like reference numerals designate corresponding parts throughout the several views.

DETAILED DESCRIPTION

In the following description, reference is made to the accompanying drawings, which form a part hereof, and in which is shown, by way of illustration, various embodiments of the present disclosure. It is understood that other embodiments may be utilized and changes may be made without departing from the scope of the present disclosure.

Theory

After significant research, the inventors of the subject disclosure, without being bound by theory, have determined that the body is believed to operate as a type of "Omic web" in which interactions of the genome, transcriptome, proteome, metabolome, and microbiome are linked and affect one another. It therefore follows that the health/disease state or disease risk of one system can be assessed by measuring certain components of a different system (e.g., the state of the genome can be assessed by measuring components of the microbiome). Extensive research, evaluation, and experimentation has revealed that certain metabolites in an individual appear to reliably and accurately determine the health/disease state or disease risk of an individual. In other words, the Omic web of an individual can be well, if not completely, described by measuring the certain metabolites of interest. Furthermore, upon assessment of these metabolites, tailored recommendations can be prepared to improve the health or disease risk of the individual.

As discussed in detail below, the disclosed systems and methods in one aspect involve the measurement and analysis of certain key metabolites of interest, in particular, indole propionic acid (IPA), indole-3-lactic acid (ILA), indole-3-acetic acid (IAA), Tryptophan (TRP), Serotonin (SER), Kynurenine (KYN), Total Indoxyl Sulfate (IDS), Tyrosine (TYR), Xanthine (XAN), 3-Methylxanthine (3MXAN) and Uric Acid (UA). 4-Hydroxybenzoic acid (4HBAC), also is believed to be a key metabolite of the gut microbiome metabolites; however, 4HBAC is somewhat unstable, and thus cannot be reliably measured. Notwithstanding, analyzing for 4HBAC can providing useful information in certain situations.

In another aspect, the disclosed system and methods involve modification and monitoring of the gut microbiome for treating deficiencies of the gut microbiome.

Example Systems and Methods

Figure 1:
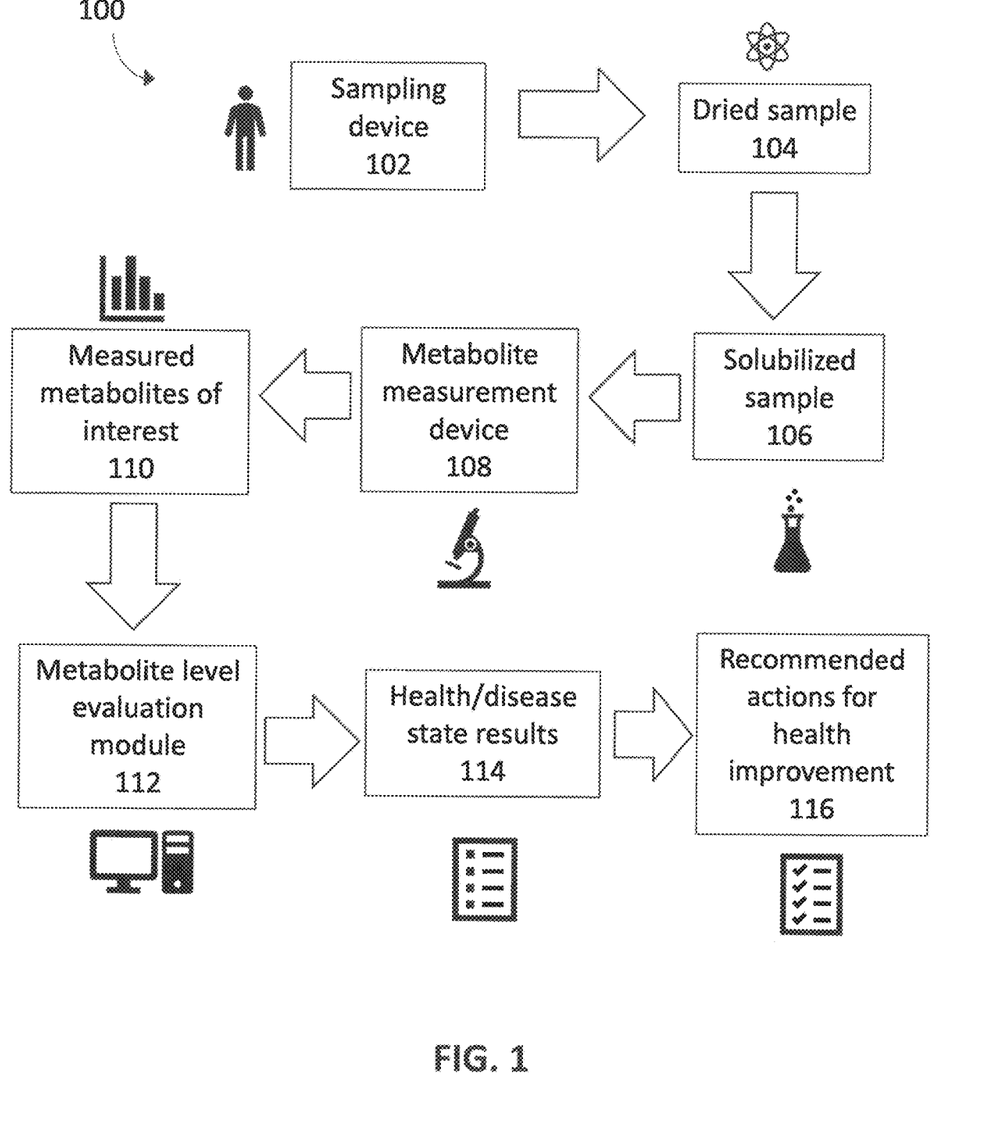
FIG. 1 shows an exemplary system for selective metabolite measurement and analysis, in accordance with some embodiments of the subject disclosure.
Figure 2:
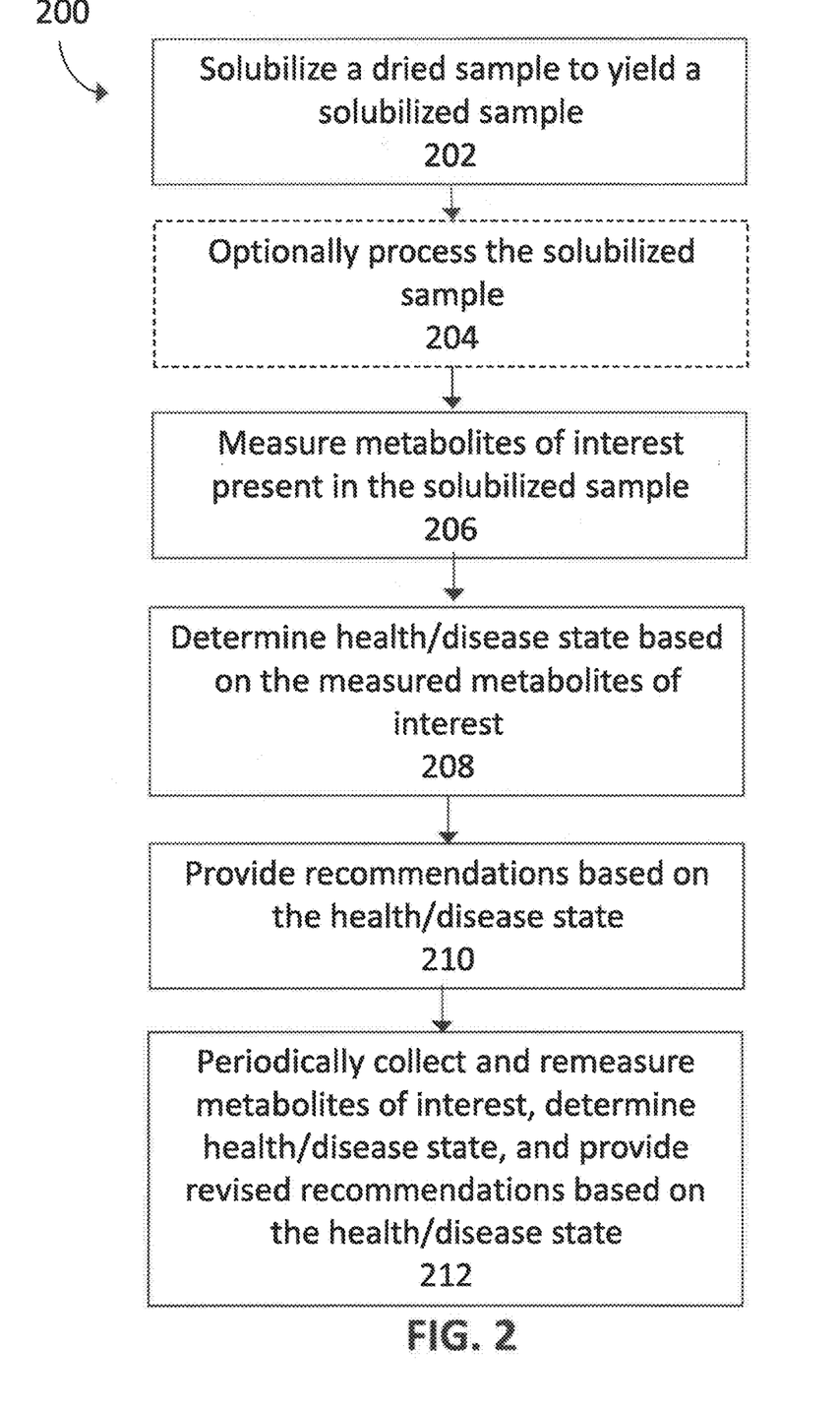
FIG. 2 shows a flow diagram of an exemplary method for testing and analyzing metabolites of interest, in accordance with some embodiments of the subject disclosure.
Figure 3A:
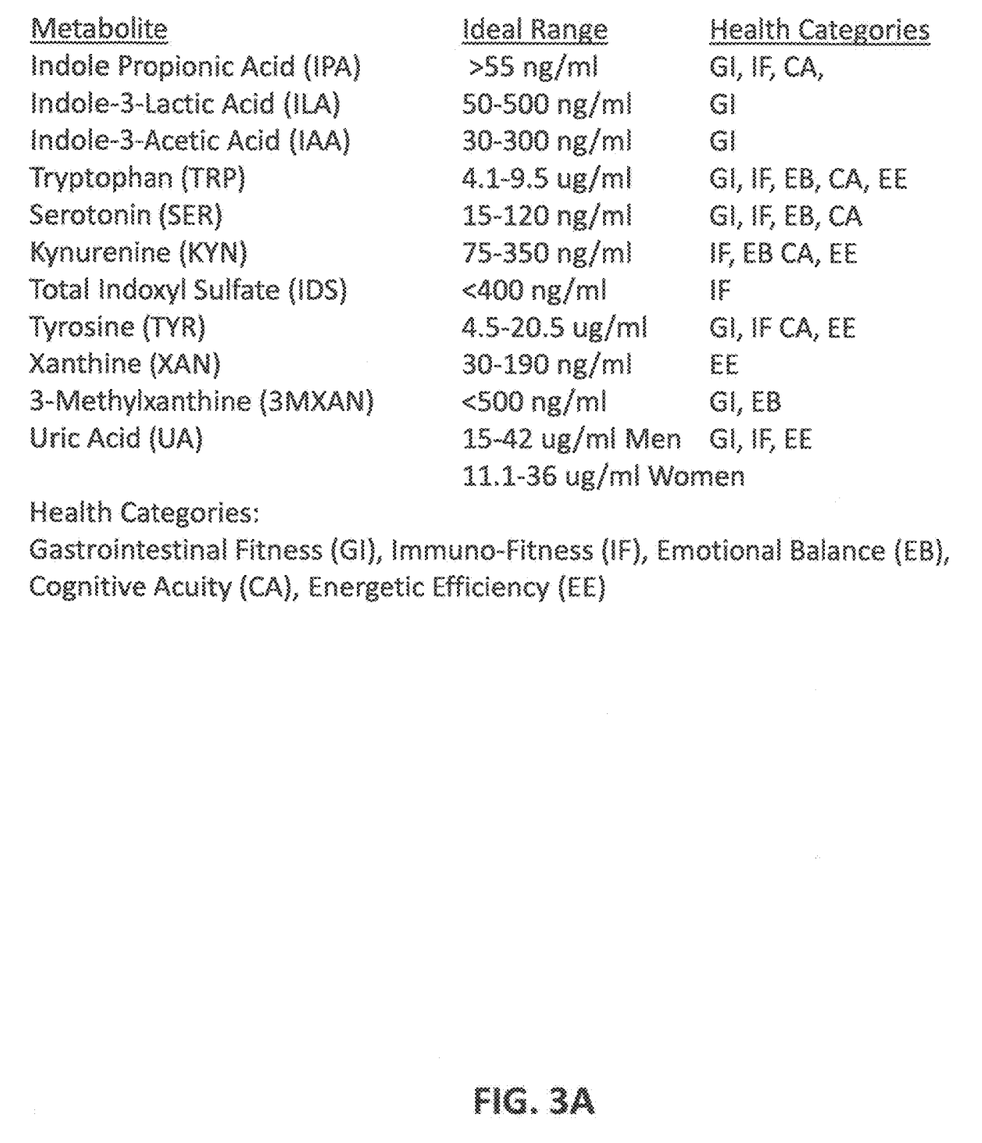
FIGS. 3A-3D show scored test reports of microbiome health of an individual in accordance with the subject disclosure.
Figure 3B:
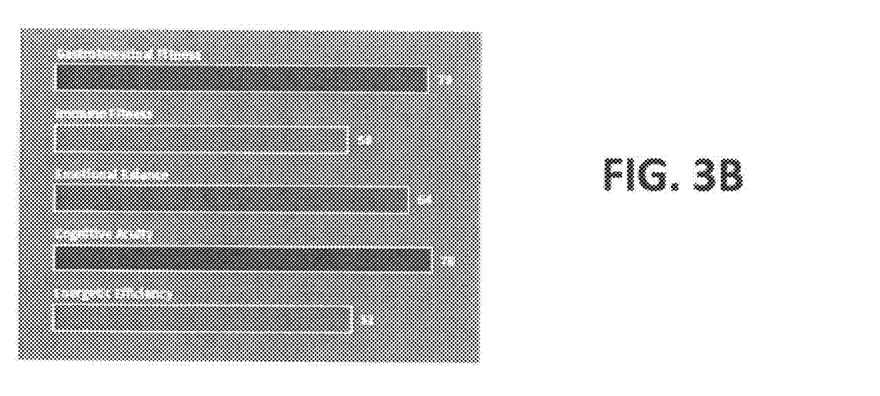
Figure 3C:
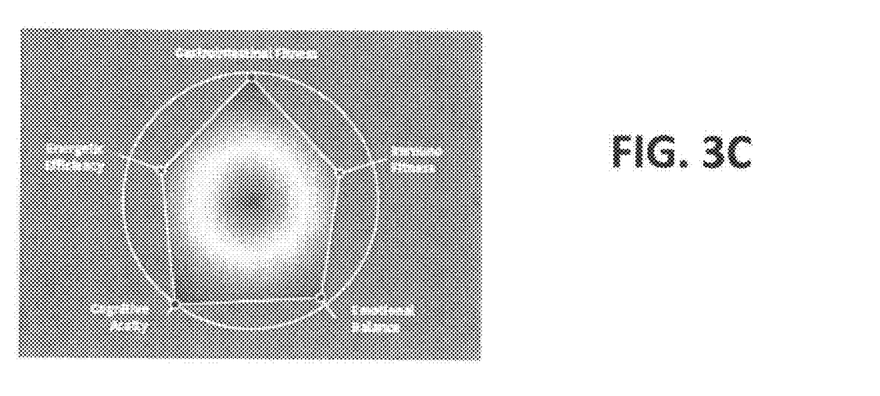
Figure 3D:
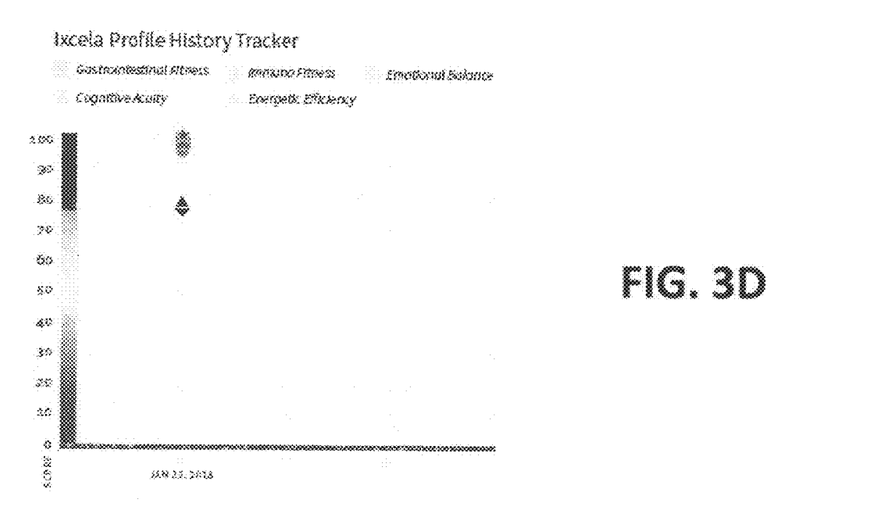

Systems and methods for measuring metabolites of interest and using the measured metabolites to evaluate an individual's health or disease state or disease risk are described herein. As used herein, the terms "health state", "disease state" and "disease risk" refer to the overall physical health of an individual, including an individual's risk for developing one or more diseases or health conditions. FIG. 1 shows an exemplary system 100 for carrying out the disclosed methods. FIG. 2 illustrates an exemplary method 200 for measuring metabolites of interest and evaluating the measured metabolite levels to assess an individual's health or disease state or disease risk. As used herein, the term "individual" means any human or non-human mammal. As shown in FIG. 1, system 100 includes a sampling device 102, which may be used to obtain a sample from an individual. Sampling device 102 may be designed to accommodate any type of sample of bodily fluid from an individual, such as a blood sample, although a urine sample and/or a saliva sample and/or a sweat sample also advantageously may be used.

In select embodiments, sampling device 102 is configured to receive a wet blood sample (e.g., with one or more layers of filter paper). In some such embodiments, the blood sample may be obtained from the individual by any method known in the art. This may include traditional venipuncture, wherein blood is obtained directly from an individual's vein. The blood may also be collected via a finger prick or via a "prick" of any other part of the individual's body. Blood collected via this method is typically obtained from blood capillaries near the surface of the skin by piercing the skin with a lancet or similar device. The blood from the "finger prick" may be collected into a capillary tube and then dispensed onto a substrate of sampling device 102. Any desired sample volume may be used, such as, for example, less than 10 mL, less than 5 mL, or, in some cases less than 1 mL. In some embodiments, sampling device 102 may allow a wet blood sample to partially or fully dry to produce a dried sample 104. In a preferred embodiment the sampling device comprises a blood sampling device as described in US 2016/0320367, the contents of which are incorporated herein by reference.

Method 200 continues with solubilizing 202 the dried sample 104 to yield a solubilized sample 106. Dried sample 104 may be solubilized 202 with any desired solvent or solvent mixture. In some embodiments, for example, deionized water, and/or other suitable solvents such as acidified acetonitrile (0.4% acetic acid in acetonitrile), may be used to solubilize 202 dried sample 104. During solubilization 202, metabolites present in dried sample 104 are transferred to solubilized sample 106. In some embodiments, solubilized sample 106 may be separate from sampling device 102 while, in other embodiments, solubilized sample 106 may be contained inside sampling device 102.

Method 200 continues with optionally processing 204 the solubilized sample 106. In some embodiments, processing 204 solubilized sample 106 may include heating, cooling, diluting, concentrating, separating, adjusting pH, and/or introducing one or more binding agents to facilitate metabolite measurement.

Method 200 continues with measuring 206 one or more of the key metabolites of interest present in solubilized sample 106. Any suitable number of metabolites of interest may be measured 206 in the disclosed methods and systems. For example, in some embodiments, several, preferably eleven or all twelve of the above mentioned key metabolites of interest may be measured. In some particular embodiments, between a minimum of two, and preferably between three and seven key metabolites of interest may be measured. In other select embodiments, 8, 9, 10, 11, or 12 of the key metabolites of interest may be measured. The key metabolites of interest are selected based on their outsized role in effecting many aspects of health, as well as their "actionability," i.e., whether action can be taken to positively modify the level of metabolite present.

The selected key metabolites of interest may be measured 206 according to any known technique, including with a metabolite measurement device 108 (as illustrated in FIG. 1). Metabolite measurement device 108 may rely on analytical chemistry techniques, such as a two column liquid chromatography (LC), followed by a 16 channel electrochemical array detector, following the teachings of my prior PCT/US98/22275 and using as an A phase solvent $0.1MLi_3PO_4$ and 0.5% Methanol, and as a B phase solvent $0.1MLi_3PO_4$ and 35% Acetonitrile. The levels of the selected metabolites of interest measured in an individual's blood sample are compiled in a chart, graph, list, or other form, and compared to standards as described below. FIG. 1 includes a chart 110 displaying measured key metabolites of interest. In select embodiments, measured levels of key metabolites of interest may be provided in machine-readable format. A summary of the measured key metabolites of interest may be provided in a format designed for a medical professional or for an individual, depending on intended application.

Method 200 continues with determining 208 heath and/or disease state based on the measured key metabolites of interest. In some embodiments, health and/or disease state of an individual can be determined using a metabolite level evaluation module 112, as shown in FIG. 1. Metabolite level evaluation module 112 may be implemented on a processor or other type of computing device. Metabolite level evaluation module 112 may, in some embodiments, be configured to receive levels of measured key metabolites of interest as an input, evaluate the measured levels of metabolite of interest, and output an analysis of health/disease state based on peer-reviewed literature which was validated and confirmed internal studies of hundreds of individuals based on their extensive health histories, and configured to calculate health category scores calculated by "weighing" certain metabolites based on their importance in that category.

In some embodiments, metabolite level evaluation module 112 may be configured to output health/disease state results 114, as shown in FIG. 1. Health/disease state and disease risk results 114 may include, in some cases, a report, a listing of the levels of the key metabolites of interest measured, and/or recommendations for modifying the gut microbiome in order to improve the health/disease state or disease risk of the individual. In particular embodiments, health/disease or disease risk state results 114 include an evaluation of one or more of the following: a summary of gut health, immune-fitness, cognitive acuity, emotional balance, and energetic efficiency.

Method 200 concludes with optionally preparing recommendations 210 based on the health/disease state or disease risk of the individual. For example, if desired, the compiled health/disease state or disease risk results 114 may include recommended actions for health improvement 116, as shown in FIG. 1. Example recommended actions for health improvement 116 include nutritional changes, more particularly ingestion of tailored supplements, and optionally also may include one or more of the following types of recommendations: physical training, sleep schedule, emotional balancing techniques (e.g., therapy, medication, etc.), and lifestyle (e.g., interventions aimed at reducing stress, improving sleep hygiene, and/or mindfulness training). The compounds measured are related in a web of interaction among themselves and among different organs, bacteria composition and environmental factors (diet, exercise, stress and medications) and the individual's underlying genetic makeup. The tests and treatment recommendations can beneficially modify everything but the final factor. In select embodiments, nutritional recommendations may relate to food groups specific to each key metabolite, feeding plans specific to energy requirements, and/or educational information regarding ways to improve the levels of key metabolites of interest present in the individual's body.

The output of the several key metabolites are then scored and compiled into the history chord of microbiome health for the tested individual, (FIGS. 3A-3D), and based on the scoring and individual concentrations of the several key metabolites as above discussed, a program including diet change, exercise and lifestyle habit changes be proposed together with tailored supplements chosen specifically to modify levels of the key metabolites, as needed. Also, a schedule is created to monitor changes in key metabolites by periodically testing and adjustment of tailored supplements until an optimal microbiome health score is achieved for the individual. Supplements include prebiotics, probiotics, viable melatonin, vitamin B complex, copper, and CoQ10 as will be discussed below.

Nutritional change recommendations include supplement recommendations, as follows:
1. (Probiotic)—Helps to support the balance the good bacteria in the gut. Biome support contains 17 species of bacteria. It is designed to help normalize interactions between the multiple species in the gut. The use of biome support is suggested when biomarkers such as IPA, IlA, IAA and IDS are found to be outside of normal, reported and cited concentrations. The use of a probiotic as a general supplement is confirmed typically by a serial testing after 2 to 3 and 6 months of use.

2. (Tryptophan)—Helps support neurotransmitter production, vitamin production and sleep. Tryptophan is only suggested to be used when dietary interventions prove to be inadequate at maintaining the appropriate relationship between the ratios of Tryptophan to Tyrosine, due to the fact that Tryptophan and Tyrosine share the same LAT1 transporter across the blood brain barrier with Branch Chain Amino Acids (BCAA) which are frequently used by athletes. This individual factor needs to be considered in the use of Tryptophan (also a precursor to sleep regulating hormones). Tryptophan is advantageously used for improving Energetic Fitness, Cognitive Acuity, Emotional Balance, Gastro Intestinal Fitness, Immuno Fitness as discussed below.

3. (5HTP and B6)—Helps support the production of neurotransmitters, gut mobility, and sleep. 5HTP and B6 are recommended when both Tryptophan and serotonin is low and certain prescription drugs are not being taken. 5HTP is the precursor for Serotonin. In situations sleep difficulties are reported problem by tryptophan is in a normal range Balance might be recommended. In the gut Tryptophan is frequently n-acetylated. N-acetyl tryptophan can proceed more easily to the pathway of melatonin. This pathway maybe adversely impacted even though Tryptophan levels are within a normal range. 5HTP and B6 are advantageously used for improving Cognitive Acuity, Emotional Balance, Immuno Fitness as discussed below.

4. (NAC (N-Acetyl-L-Cysteine)+L-Methionine+Selenium)—Strong antioxidants used to help with energetic efficiency, very useful for high intensity athletes. These are cofactors for many enzymes in the tryptophan pathway particularly in the branch related to kynurenine metabolism. That branch is driven towards compounds which are neuroprotective by enzymes for which selenium is a cofactor. That same pathway is also related to the production of compounds that are involved in mitochondrial function bringing ADP to ATP which is the principle energetic source for muscular function. Selenium is recommended when the KYN/TRYP relationship is abnormally high. These supplements are advantageously used for improving Energetic Fitness, Emotional Balance, Immuno Fitness as discussed below.

5. (Melatonin) Helps with sleep. Is the principle sleep hormone. If problems associated with sleep dysfunction are not resolved first with diet and exercise intervention, then with probiotic, tryptophan, 5HTP utilization Melatonin would be recommended to directly affect sleep function. Melatonin is advantageously used when individual indicates issues with sleep.

6. (Vit. B complex)—B vitamins have a direct impact on your energy levels, brain function, and cell metabolism. Vitamin B complex helps prevent infections and helps support or promote: cell health. Vitamin B's are the direct precursors to NAD and NADH, which are critical factors in the enzyme complex that drive the generation of energy in mitochondria. They also play an important role in regulating kynurenine in the tryptophan pathway. Vitamin B is advantageously used for improving Energetic Fitness, Cognitive Acuity, Emotional Balance, Gastro Intestinal Fitness, Immuno Fitness as discussed below.

7. (Vitamin C+Zinc). Antioxidant and mineral that helps support a healthy immune system. If there is evidence of oxidative stress through high 4HBAC, Indoxyl sulfate, and uric acid Vitamin C and zinc will mediate against the effects of free radical effect of other biochemical systems. Vitamin C+Zinc is advantageously used for improving Energetic Fitness, Cognitive Acuity, Gastro Intestinal Fitness, Immuno Fitness as discussed below.

Numerous variations are possible, depending on the intended audience for the recommended actions for health improvement 116 as will be discussed below.

Periodically, fresh blood samples are taken from an individual, the blood samples processed and metabolites measured as before, revised recommendation are provided based on the health/disease state of the individual, and the process is again repeated periodically at 212.

Figure 4:
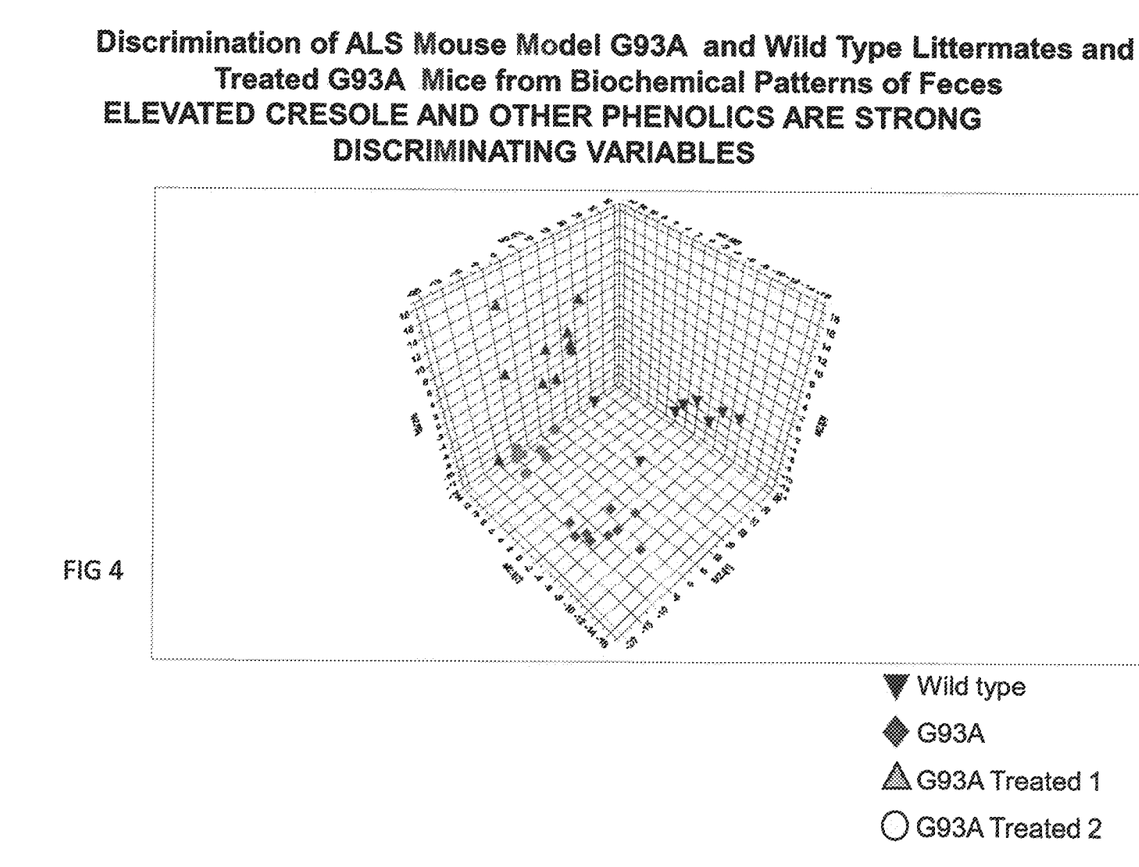
FIG. 4 is a three-dimensional graph of patterns of biochemical measurements of ALS Mouse and Wild type littermate and treated mice samples.

Further illustrative of the invention is seen in FIG. 4 which a three dimensional graph illustrating measurements of feces samples of elevated cresol and other phenolics of ALS mouse models treated mouse models and wild type littermates. And, FIGS. 5A and 5B graphs IPA measurements of wild type and gene positive Huntington's Disease mouse models from feces.

Figure 5A:
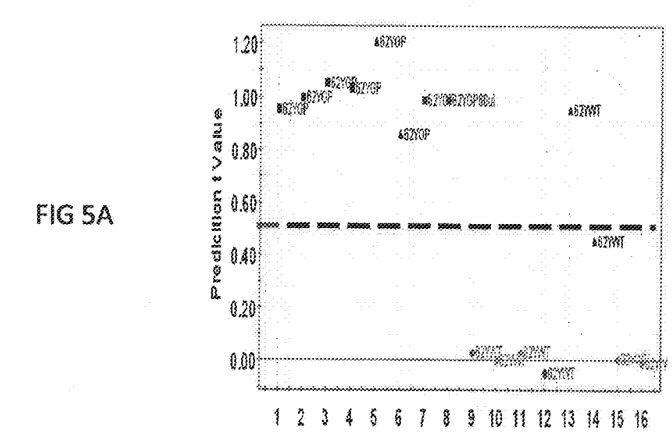
FIGS. 5A and 5B are graphs of IPA measurements of wild type and gene positive HD mouse models.
Figure 5B:
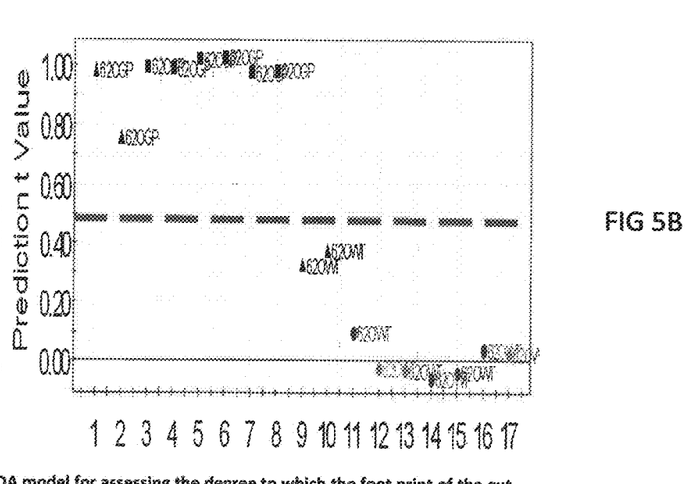

FIG. 5A shows one of a series of (two out) tests of the PLS-DA model for assessing the degree to which the foot print of the gut microbiome reflected in the dry weight normalized coordinately bound LCECA patterns of feces allows categorization of young 19 day littermate WT and GP CAG140 mice. Training sets of 8 and validation sets of 2 are sequentially evaluated for all samples. In the example shown both GP and one WT were correctly classified. A similar model for old 90 day WT and GP CAG140 mice is shown in FIG. 5B where three were correctly classified. Overall for the young and old categories CCR is 0.93 and 0.86 respectively. Thus, we can currently categorize genetic status of a mouse by its microbiome foot print about 90% of the time even prior to any symptoms.

Further details of the present disclosure are given in the following example of metabolite measurements and recommended supplements:

A) Gastro Intestinal Fitness

Supplements recommended:
1. Probiotic if tryptophan, tyrosine, ILA and IAA are high, and if IPA, ILA and IAA are low
2. Typtophan if Tryptophan low
3. 5HTP and B6 if serotonin is low
4. Vitamin C and Zinc if Tyrosine is low and Uric acid is High B) Immuno Fitness Supplements might be recommended:
1. Probiotic if Tryptophan and Indoxyl sulfate are high, or if IPA and serotonin are low
2. Tryptophan if Tryptophan is low
3. Vitamin B complex if KYN is high
4. 5HTP and B6 if serotonin is low
5. NAC+L-Methionine+Selenium if KYN is high
6. Vitamin C and Zinc if Tyrosine is low and Uric acid is High Supplements recommended:
1. Probiotic if tryptophan is high and Serotonin is low
2. Tryptophan if Tryptophan or serotonin is low
3. Vitamin B complex if KYN is high
4. 5HTP and B6 if serotonin is low
5. Vitamin C and Zinc if KYN is high C) Cognitive Acuity Supplements recommended
1. Probiotic if tryptophan and tyrosine are high and IPA and Serotonin are low 2. Vitamin C and Zinc if Tyrosine is high
3. Tryptophan if Tryptophan or serotonin is low
4. Vitamin B complex if Kyn is high
5. 5HTP and B6 if serotonin is low Supplements that might be recommended
1. Probiotic if tryptophan and tyrosine are high
2. Vitamin C and Zinc if xanthine, tyrosine, or uric acid are high
3. Tryptophan if Tryptophan is low
4. Vitamin B complex if KYN is high
5. NAC plus LMethionine and Selenium if Xanthine is high Following are blood test results, before and after, if various individuals based on administration of various supplements.

Individual 1 was given a specially designed 17 strain Probiotic, had diet modifications suggested and supplements of Vitamin C, zinc, CoQ10, B complex were added. This helped to lower Indoxyl Sulfate, Kynurenine, Xanthine Individual 2 was given a specially designed 17 strain Probiotic, had diet modifications suggested and supplements of Vitamin C, zinc, CoQ10. Lowered Xanthine and IDS and raised IPA.

Individual 3 was given a specially designed 17 strain Probiotic and supplements of Vitamin C, zinc, CoQ10. Lowered Indoxyl sulfate and Xanthine Individual 4 was given supplements of Vitamin C, zinc, CoQ10. Lowered Xanthine. Individual 5 was given a spe-

| | Metabolite Unit | 3MX ng/ml | IAA ng/ml | ILA ng/ml | IPA ng/ml | IDS ng/ml |
|---|---|---|---|---|---|---|
| | Normal | <500 | 30-300 | 50-500 | >55 | <400 |
| Indiv. 1 | Before[1] | 86.09 | 141.25 | 129.45 | 203.11 | 315.65 |
| | After | 6.21 | 92.5 | 91.16 | 117.25 | 274.54 |
| Indiv. 2 | Before[2] | 54.84 | 145.08 | 123.50 | 51.76 | 409.55 |
| | After | 32.68 | 167.81 | 125.67 | 100.16 | 357.57 |
| Indiv. 3 | Before[3] | 36.07 | 228.97 | 123.35 | 129.94 | 497.11 |
| | After | 5.17 | 169.51 | 91.2 | 537.27 | 157.68 |
| Indiv. 4 | Before[4] | 33.2 | 154.47 | 113.4 | 142.41 | 233.62 |
| | After | 69.04 | 121.55 | 93.74 | 85.22 | 333.65 |
| Indiv. 5 | Before[5] | 25.38 | 138.72 | 87.64 | 44.57 | 146.84 |
| | After | 104.88 | 87.23 | 117.54 | 61.66 | 236.79 |
| Indiv. 6 | Before[6] | 21.44986478 | 139.0087441 | 64.89523 | 37.2547 | 215.4566 |
| | After | 17.61423478 | 205.2114178 | 96.49815 | 57.22367 | 227.9377 |
| Indiv. 7 | Before[7] | 80.95 | 131.70 | 109.46 | 52.552 | 489.62 |
| | After | 171.992 | 156.698 | 65.428 | 71.62 | 332.48 |
| Indiv. 8 | Before8 | 83.23 | 118.45 | 70.11 | 45.62 | 228.80 |
| | After | 64.93 | 138.45 | 67.69 | 54.29 | 361.55 |
| Indiv. 9 | Before[9] | 110.19 | 97.31 | 32.73 | 87.41 | 272.04 |
| | After | 107.18 | 127.90 | 44.35 | 165.35 | 109.00 |
| Indiv. 10 | Before[10] | 19.26672 | 132.6309 | 57.73866 | 12.73788 | 92.22044 |
| | After | 132.9447 | 123.946 | 60.5723 | 24.7631 | 168.1507 |

| | Metabolite Unit | KYN ng/ml | serotonin ng/ml | tryptophan µg/ml | Tyrosine µg/ml | uric acid µg/ml | xanthine ng/ml |
|---|---|---|---|---|---|---|---|
| | Normal | 75-350 | 15-120 | 4.1-9.5 | 4.5-20.5 | 15-42 | 30-190 |
| Indiv. 1 | Before | 356.69 | 82.68 | 7.25 | 9.69 | 21.05 | 248.99 |
| | After | 233.29 | 82.45 | 6.04 | 7.46 | 19.46 | 156.25 |
| Indiv. 2 | Before | 186.66 | 61.20 | 7.22 | 10.94 | 30.12 | 233.86 |
| | After | 209.94 | 75.19 | 7.27 | 8.91 | 30.99 | 130.94 |
| Indiv. 3 | Before | 218.01 | 68.08 | 7.01 | 8.59 | 27.38 | 221.81 |
| | After | 206.62 | 70.27 | 6.45 | 6.52 | 28.89 | 184.37 |
| Indiv. 4 | Before | 301.62 | 48.23 | 8.47 | 11.45 | 24.61 | 222.94 |
| | After | 285.79 | 49.07 | 6.75 | 8.14 | 26.21 | 165.99 |
| Indiv. 5 | Before | 256.41 | 28.09 | 6.44 | 9.16 | 15.9 | 330.96 |
| | After | 202.89 | 42.74 | 8.01 | 14.16 | 19.9 | 144.6 |
| Indiv. 6 | Before | 163.8883 | 17.41096 | 6.922951 | 8.830608 | 20.34835 | 140.299 |
| | After | 169.4513 | 21.07541 | 6.619294 | 6.584736 | 16.86458 | 148.6497 |
| Indiv. 7 | Before | 671.44 | 196.33 | 7.16 | 11.65 | 28.71 | 188.35 |
| | After | 135.92 | 30.354 | 5.028 | 6.65 | 13.19 | 80.456 |
| Indiv. 8 | Before | 280.60 | 7.63 | 4.26 | 7.75 | 21.59 | 96.20 |
| | After | 244.80 | 47.30 | 4.50 | 7.23 | 20.29 | 83.65 |
| Indiv. 9 | Before | 161.91 | 29.09 | 5.07 | 7.94 | 13.47 | 86.72 |
| | After | 196.80 | 39.45 | 5.74 | 9.68 | 14.92 | 98.03 |
| Indiv. 10 | Before | 156.2026 | 47.10654 | 5.63586 | 7.49808 | 27.86688 | 103.0789 |
| | After | 167.968 | 52.4378 | 6.1306 | 10.0195 | 29.6989 | 182.7638 |

[1] Probiotic, diet modifications and VitC, zinc, CoQ10, B complex
[2] Probiotic, diet modifications and VitC, zinc, CoQ10
[3] Probiotic, and VitC, zinc, CoQ10
[4] VitC, zinc, CoQ10
[5] Probiotic, and VitC, zinc, CoQ10
[6] probiotic
[7] Probiotic, vit B complex
[8] Probiotic, 5HTP
[9] probiotic
[10] probiotic cially designed 17 strain Probiotic and supplements of Vitamin C, zinc, CoQ10. Lowered xanthine, raised IPA and serotonin Individual 6 was given a specially designed 17 strain Probiotic. Began to raise levels of serotonin and IPA Individual 7 was given a specially designed 17 strain Probiotic and supplemented with vitamin B complex. Lowered Kynurenine, serotonin and Indoxyl sulfate and raised IPA.

Individual 8 was given a specially designed 17 strain Probiotic and supplement 5HTP. Raised serotonin and IPA.

Individual 9 was given a specially designed 17 strain Probiotic. Lowered Indoxyl sulfate, raise IPA and ILA.

Individual 10 was given a specially designed 17 strain Probiotic. Raised IPA

Various changes may be made without departing from the spirit and scope of the disclosure. All such modifications and variations are intended to be included herein within the scope of this disclosure and the present disclosure and protected by the following claims.

What is claimed is:

1. The method for improving the gut health, emotional balance, cognitive acuity, energetic efficiency and immuno fitness of an individual in need of improvement, the method consisting of the steps in sequence of:
   (1) collecting fluid samples from said individual;
   (2) analyzing said fluid samples for concentration of the following microbiome modified compounds in the fluid samples: indole propionic acid (IPA), indole-3-lactic acid (ILA), indole-3-acetic acid (IAA), Tryptophan (TRP), Serotonin (SER), Kynurenine (KYN), Total Indoxyl Sulfate (IDS), Tyrosine (TYR), Xanthine (XAN), 3-Methylxanthine (3MXAN) and Uric Acid (UA);
   (3) comparing the concentration of said microbiome modified compounds to standards concentrations;
   (4) providing for oral administration to said individual one or more supplements selected from the group consisting of a prebiotic, a probiotic, a vitamin B complex, and CoQ10 protocol to raise or reduce the concentration, as the case may be, of components of the gut microbiome of said individual that effect the one or more microbiome modified compounds that have measured concentrations that fall outside of the standards concentrations; and
   (5) repeating steps (1) to (4) to bring the measured concentrations to within the standards concentrations.

2. The method according to claim 1, wherein said liquid samples comprise blood.

3. The method according to claim 1, wherein said liquid samples comprise urine.

4. The method according to claim 1, wherein said liquid samples comprise tears.

5. The method according to claim 1, wherein two or more supplements selected from the group consisting of a prebiotic, a probiotic, a vitamin B complex, and CoQ10 are administered.

6. The method according to claim 1, wherein said standards concentrations are created by collecting and analyzing fluid samples from a plurality of different individuals.

* * * * *